United States Patent [19]
Wagner et al.

[11] Patent Number: 5,519,116
[45] Date of Patent: May 21, 1996

[54] PEPTIDES REPRESENTING PERMUTATIONS OF THE MASTOPARAN SEQUENCE

[75] Inventors: Thomas Wagner; Cristina Oppi, both of Rome, Italy

[73] Assignee: Enichem S.p.A., Milan, Italy

[21] Appl. No.: 961,837

[22] Filed: Oct. 16, 1992

[30] Foreign Application Priority Data

Oct. 21, 1991 [IT] Italy .................. MI91A2770

[51] Int. Cl.$^6$ .................................................. C07K 7/08
[52] U.S. Cl. .......................................... 530/327; 530/326
[58] Field of Search .................................. 530/327, 326; 514/14, 13

[56] References Cited

PUBLICATIONS

Communication and European Search Report in Corresponding European Patent Application No. 92203174.5.

Ken Nagashima et al, "Role Of Lysine Residue At 7th Position Of WASP Chemotactic Peptides," Biochemical and Biophysical Research Communications, vol. 168, No. 2, pp. 844–849 (Apr. 30, 1990).

Yuko Hirai et al, "A New Mast Cell Degranulating Peptide 'Mastoparan' In The Venom of *Vespula Lewisii*," Chem. Pharm. Bull., vol. 27, No. 8, pp. 1942–1944 (1979).

Cristina Oppi et al, "Attenuation of Gtpase Activity Of Recombinant $G_o\alpha$ By Peptides Representing Sequence Permutations of Mastoparan," Proc. Natl. Acad. Sci. USA, vol. 89, No. 17, pp. 8268–8272 (Sep. 1992).

Goate, A., Chartier–Harlin, M.–C., Mullan, M. Brown, J., Crawford, F., Fidani, L., Giuffra, L., Haynes, A., Irving, N., James, L., Mant, R., Newton, P., Rooke, K., Roques, P., Talbot, C., Pericke–Vance, M., Roses, A., Williamson, R., Rossor, M., Owen, M. and Hardy, J., *Nature*, 349 (1991), 704–706.

Higashijima, T., Usu, S., Nakajima, T. and Ross, E. M., *J. Biol. Chem.*, 263 (1988), 6401–6494.

Oppi, C., Wagner, T., Crisari, A., Camerini, B. and Tocchini Valentini, G. P., *Proc. Natl. Acad. Sci. USA*, 89 (1992), 8268–8272.

Higashijima, I., Burnier, J. and Ross, E. M. *J. Biol. Chem.*, 265 (1990), 14176–14186.

Cheung, A. H., Huang, R. –R. C., Graziano, M. P. and Strader, C. D., *FEBS Lett.*, 279 (1991), 277–280.

Okamoto, T., Murayama, Y., Hayashi, Y., Inagaki, M., Ogata, E. and Nishimoto, I., *Cell*, 67 (1991), 723–730.

Bauer, P. H., Mueller, S., Puzicha, M., Pippig, S., Obermaier, B., Heimreich, E. J. M. and Lohse, M. J., *Nature*, 358 (1992), 73–76.

Selkoe, D. J., *Cell*, , 58 (1989), 611–612.

Dyrks, T., Weidemann, A., Multhaup, G., Salbaum, J. M., Lemaire, H. –G., Kang, J., Mueller–Hill, B., Masters, C. L., and Beyreuther, K., *Embo J.*, 7 (1988), 949–957.

Nishimoto, I., Okamoto, T., Matsuura, Y., Takahashi, S., Okamoto, T., Murayama, Y. and Ogata, L., *Nature*, 362 (1993), 75–79.

Oppi, C. et al; PNAS 89, 8268–8272, 1992.

Higashijima, T. et al.; JBC 265, 14176–14186, 1990.

Argiolas, A et al, JBC 259, 10106–10111, 1984.

*Primary Examiner*—Christina Y. Chan
*Attorney, Agent, or Firm*—Oblon, Spivak, McClelland, Maier & Neustadt

[57] ABSTRACT

New peptides representing permutations of the mastoparan sequence are described. The peptides may be of pharmaceutical interest in counteracting pathologies due to alterations in the interaction between membrane receptors and G-proteins.

4 Claims, 3 Drawing Sheets

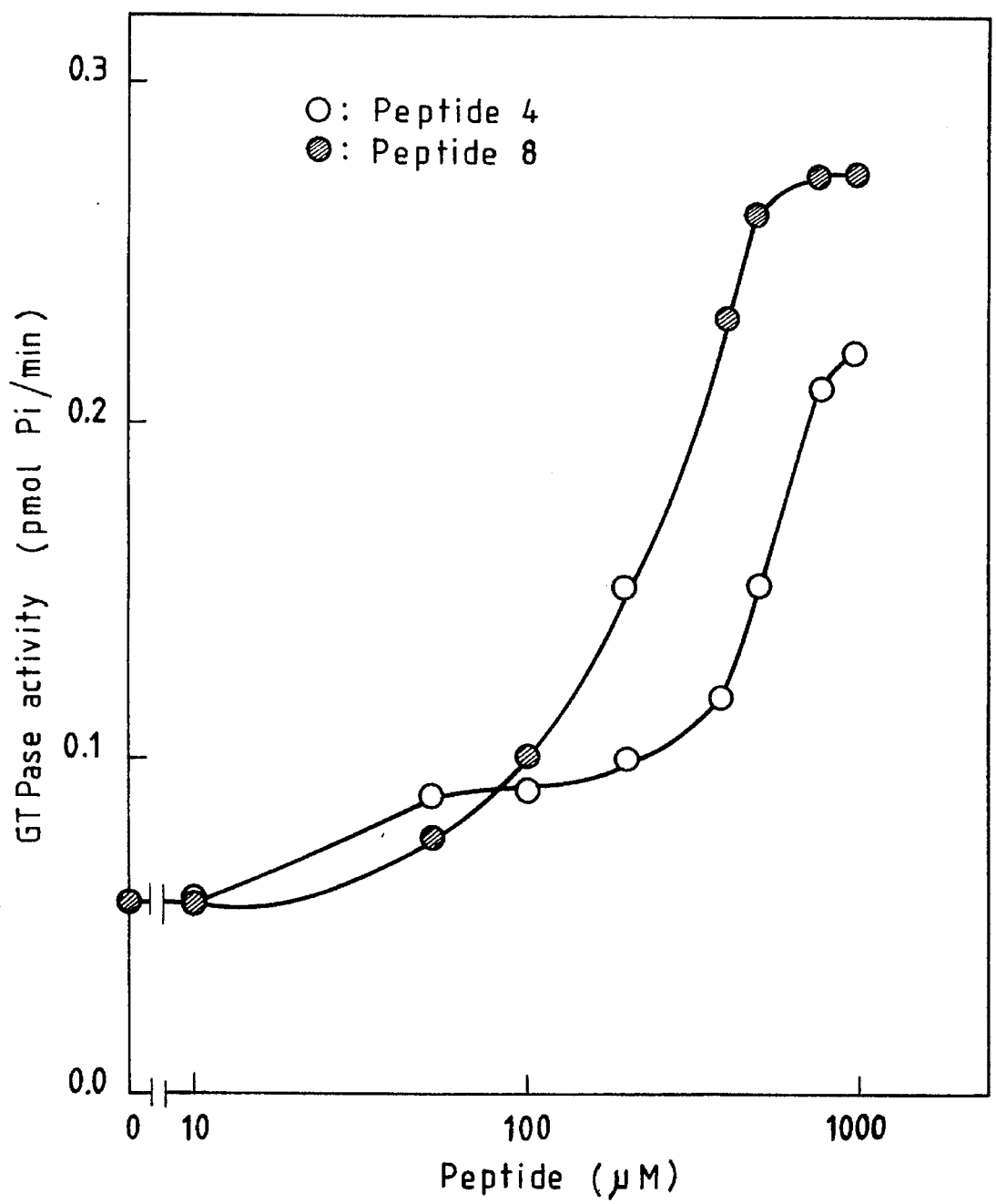

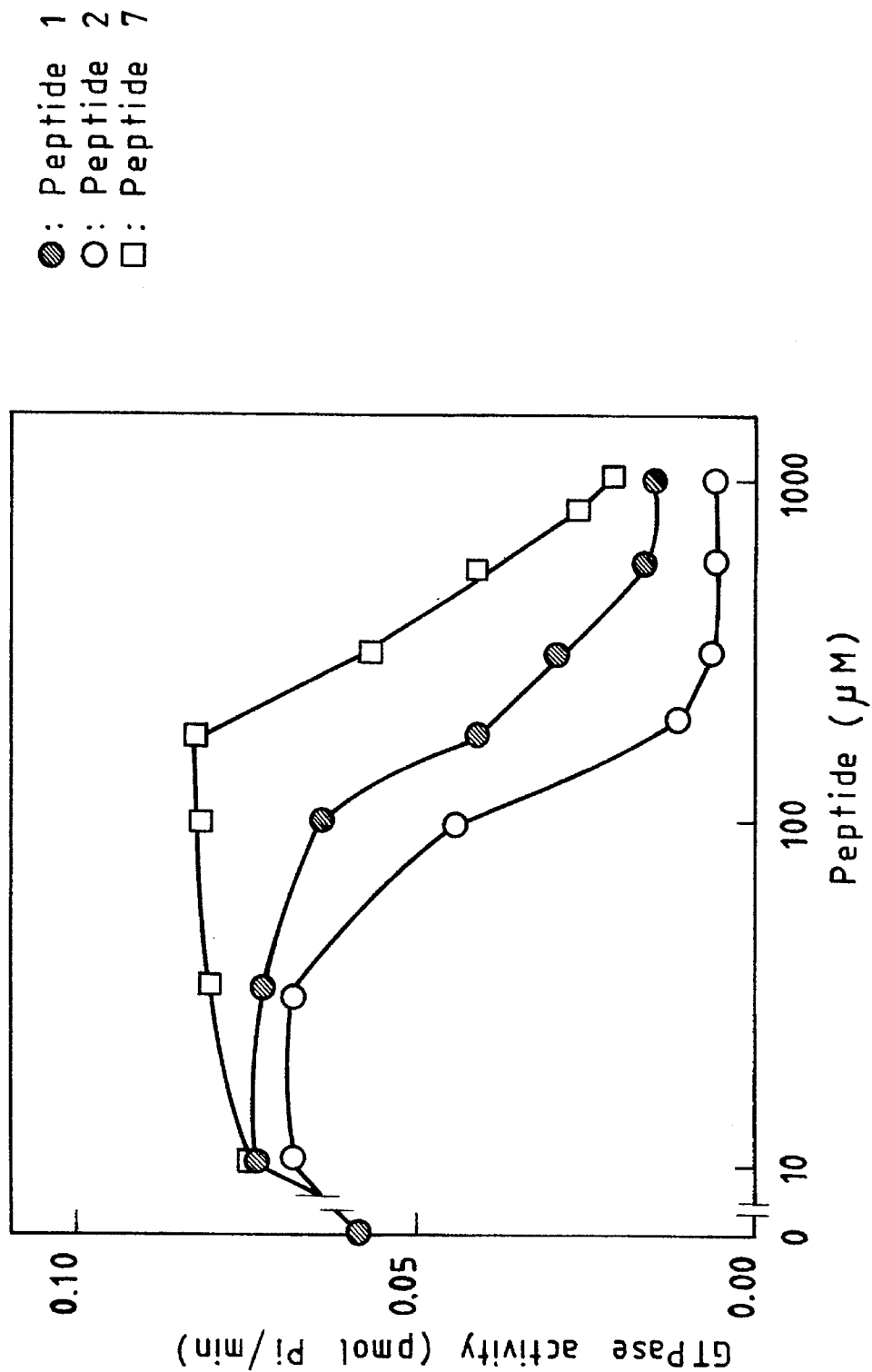

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 14 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:1:

```
Ala  Leu  Ala  Ile  Lys  Leu  Ile  Leu  Asn  Leu  Lys  Ala  Lys  Ala
 1                  5                        10
```

( 2 ) INFORMATION FOR SEQ ID NO:2:

( i ) SEQUENCE CHARACTERISTICS:
      ( A ) LENGTH: 14 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:2:

```
Leu  Lys  Ile  Ala  Leu  Asn  Leu  Lys  Ala  Leu  Ile  Ala  Ala  Lys
 1                  5                        10
```

( 2 ) INFORMATION FOR SEQ ID NO:3:

( i ) SEQUENCE CHARACTERISTICS:
      ( A ) LENGTH: 14 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:3:

```
Asn  Ala  Ala  Leu  Ile  Ala  Lys  Leu  Leu  Lys  Ala  Lys  Leu  Ile
 1                  5                        10
```

( 2 ) INFORMATION FOR SEQ ID NO:4:

( i ) SEQUENCE CHARACTERISTICS:
      ( A ) LENGTH: 14 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:4:

```
Ile  Asn  Leu  Ala  Ala  Leu  Lys  Lys  Leu  Ala  Ala  Lys  Ile  Leu
 1                  5                        10
```

( 2 ) INFORMATION FOR SEQ ID NO:5:

( i ) SEQUENCE CHARACTERISTICS:
      ( A ) LENGTH: 14 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:5:

```
Ile  Asn  Leu  Ala  Lys  Ala  Ala  Leu  Lys  Ala  Leu  Lys  Ile  Leu
```

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:6:

```
Lys  Ile  Leu  Ile  Asn  Leu  Lys  Ala  Leu  Ala  Ala  Leu  Ala  Lys
1                     5                          10
```

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:7:

```
Leu  Asn  Ala  Lys  Leu  Lys  Ala  Ile  Ala  Leu  Ala  Leu  Ile  Lys
1                     5                          10
```

(2) INFORMATION FOR SEQ ID NO:8:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:8:

```
Asn  Ile  Leu  Ala  Leu  Ala  Lys  Ala  Leu  Ile  Lys  Ala  Leu  Lys
1                     5                          10
```

(2) INFORMATION FOR SEQ ID NO:9:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:9:

```
Asn  Ala  Lys  Ile  Leu  Ala  Leu  Leu  Ala  Leu  Ile  Lys  Ala  Lys
1                     5                          10
```

PEPTIDES REPRESENTING PERMUTATIONS OF THE MASTOPARAN SEQUENCE

This invention relates to new peptides representing permutations of the mastoparan sequence.

These peptides can be used in the preparation of medicaments for the treatment of disorders such as hypothyroidism, asthma and endocrinic tumours of the hypophysis.

The hope of being able to solve the problem of treating said disorders has for some time resided in substances able to interfere with or detect the pathological transmission of signals from the outside to the inside of the cells. In particular, attention has been directed towards those compounds able to block signal transmission at the G-protein level. These substances could be of great pharmaceutical interest in counteracting pathologies due to alterations in the interaction between membrane receptors and G-proteins. In this respect it has been demonstrated that tissues suffering from such pathologies present abnormal G-proteins (Harvey A., 1991, Trends Pharmacol. Sci., 12, 317–319; Landis et al., 1989, Nature, 340, 692–696; Lyons et al., 1990, Science, 249, 655–659).

In recent years, knowledge deriving from the study of transmembranic receptor-G-protein interactions has undergone considerable development.

In particular, research on the hydrolysis of GTP by G-proteins associated with membrane receptors has shown that said hydrolysis takes place via the following sequence of events:

formation of the membrane receptor-ligand complex
activation of the G-protein bound to the receptor
formation of the GTP-G-protein α subunit complex
interaction of the complex with an effector
hydrolysis of GTP to GDP The study has resulted in the availability of various peptides, the synthesis of which was necessary in order to identify the sites of the receptors associated with the G-proteins, and has enabled their function/structure relationship to be analyzed via their capacity to modify GTPase activity (Higashijima et al., 1990, J. Biol. Chem., 265, 14176–14186; Muench et al., 1991, Eur.J. Biochem, 198, 357–364; Cheung et al., 1991, FEBS Lett.,279,277–280). Substances and peptides able to stimulate hydrolysis of GTP to GDP by G-proteins have already been identified. However substances able to inhibit this activity have not been identified.

The synthesis of peptides which inhibit the GTPase activity of G-proteins and are able to compete for these with stimulator peptides has been achieved for the first time by the authors of the present invention.

In particular, the present invention relates to new tetradecapeptides in the form of permutations of the mastoparan sequence, and represented by the following formulas:

| | |
|---|---|
| A—L—A—I—K—L—I—L—N—L—K—A—K—A | (1; SEQ ID NO:1) |
| L—K—I—A—L—N—L—K—A—L—I—A—A—K | (2; SEQ ID NO:2) |
| N—A—A—L—I—A—K—L—L—K—A—K—L—I | (3; SEQ ID NO:3) |
| I—N—L—A—A—L—K—K—L—A—A—K—I—L | (4; SEQ ID NO:4) |
| I—N—L—A—K—A—A—L—K—A—L—K—I—L | (5; SEQ ID NO:5) |
| K—I—L—I—N—L—K—A—L—A—A—L—A—K | (6; SEQ ID NO:6) |
| L—N—A—K—L—K—A—I—A—L—A—L—I—K | (7; SEQ ID NO:7) |
| N—I—L—A—L—A—K—A—L—I—K—A—L—K | (8; SEQ ID NO:8) |
| N—A—K—I—L—A—L—L—A—L—I—K—A—K | (9; SEQ ID NO:9) | where A=alanine, I=isoleucine, K=lysine, L=leucine, N=asparagine.

BRIEF DESCRIPTION OF THE DRAWINGS

FIG. 2 shows the results of a GTPase activity assay for peptides 4 and 8 of the present invention; and FIG. 3 shows the results of a GTPase activity assay for peptides 1, 2 and 7 of the present invention.

DETAILED DESCRIPTION OF THE PREFERRED EMBODIMENTS

Figure 1:
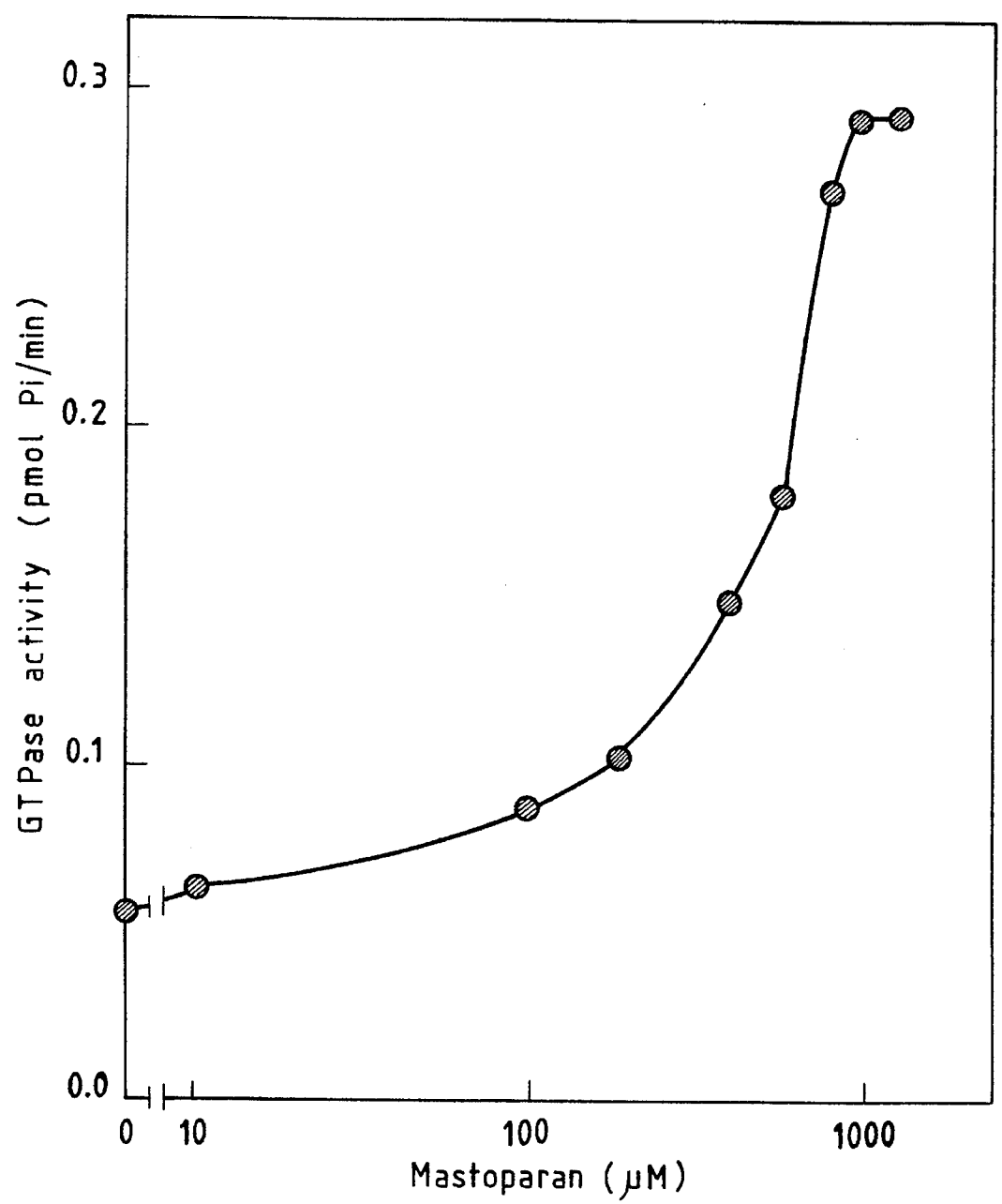
FIG. 1 shows the results of a GTPase activity assay for mastoparan.

Many of the procedures currently used for peptide synthesis are based on the solid phase method of Merrifield (1963) J. Am. Chem. Soc., 85, 2149–2154.

The peptides of the present invention were synthesized in accordance with the protocols reported by Houghten et al., (1980) Int. J. Pept. Protein Res., 16, 311–320; (1984) Eur. J. Biochem., 145, 157–162; (1985) Proc. Nat. Acad. Sci. USA, 82, 5131–5135 which represent variations of the original Merrifield method, and were obtained as C-terminal carboxylic acids.

The activity of the peptides was determined by evaluating the quantity of GTP hydrolyzed in the presence of a recombined Goα protein, using the procedures published by Brandt et al., (1983), Biochemistry, 22, 4357–4362 and by Higashijima et al., (1987), J. Biol. Chem., 262, 757–761.

An alternative method for measuring peptide activity is to evaluate the rate of GTP dissociation by the protein. This method is described by Higashijima et al., (1990), J. Biol. Chem., 265, 14176–14186.

During the course of their research, the authors of the present invention synthesized the peptides 1–9 (SEQ ID NOS:1–9) and evaluated their capacity to activate the protein rGoα. The results showed that peptides 4 (SEQ ID NO:4) and 8 (SEQ ID NO:8) considerably improve the GTPase activity of rGOα. In particular, peptide 4 (SEQ ID NO:4) has activity similar to mastoparan and peptide 8 (SEQ ID NO:8) is twice as effective. Peptides 5 (SEQ ID NO:5) and 6 (SEQ ID NO:6) are unable to activate rGOα. Surprisingly, peptides 1 (SEQ ID NO:1), 2 (SEQ ID NO:2) and 7

(SEQ ID NO:7) proved to inhibit the GTPase activity of the G-protein and, in subsequent experiments, to compete effectively with the stimulator peptides.

This discovery has no precedents and is of great importance in the search for medicaments for treating hypothyroidism, asthma and terminal endocrinic tumours.

The tests described in the examples were conducted in the following manner.

The mastoparan used was acquired from Sigma.

The lyophilized peptide powders were maintained at 20° C.

Before the experiments the peptides (including the mastoparan) were purified by HPLC using a Merck Licrospher 300 RP18 semi-preparative column (10×250 mm) and a linear gradient of acetonitrile in 0.1% of acetic acid (45%–50%, 20 min, at 2 ml/min).

The eluates containing the peptides (evaluated by absorbance at 230 nm) were evaporated to dryness in a Speed Vac (Savant) evaporator, dissolved in a little bidistilled water and again evaporated to dryness.

The subsequent analysis of each peptide by HPLC using a Beckman 4.6×250 mm Ultrasphere ODS column and applying the aforesaid gradient at 2 ml/min showed the presence of a single absorbance peak at 205 nm, as required.

The integrity and identity of the peptides were further established by amino acid analysis.

The peptide concentration in aqueous solution was determined by measuring absorbance at 205 nm in accordance with Scopes, (1974) Anal. Biochem., 59, 277–282.

The rGOα was produced by the authors of the present invention by expression in *E.coli* of the cDNA of the α subunit of the Go protein present in the rat's brain, inserted in register in the bacterial plasmid pt7-7 (Tabor et al., 1985, Proc. Natl. Acad. Sci. USA, 82, 1074–1078).

Compared with natural GOα, rGOα has an N-terminal deletion of 11 amino acids, replaced by another 5 different amino acids because of the cloning strategy adopted. The molecular weight of rGOα is 38.6 Kd.

Purification was conducted to near homogeneity, and identification was via specific antibodies for the C-terminal decapeptide of GOα (Mullaney et al., 1988, Biochem. J., 256, 649–656).

The rGOα binds GTP$_\gamma$S to saturation with a Kd of 2.9 nM at 20° and hydrolyzes GTP with a molar turnover of 0.09 min$^{-1}$ at 20° in the presence of a detergent (LUBROL 0.1%). When the rGOα is reconstituted into phospholipid blisters (by incubation with a phospholipid mixture at 4° C. for 16 hours), its basal GTPase activity reduces to 0.02 min$^{-1}$, This experimental condition which approaches that of the natural protein, in the inactivity state, inserted into the cell membrane was chosen to evaluate the effect of the peptides on the hydrolysis of GTP by rGOα.

The following examples are provided to demonstrate that described in the present invention. The purpose of the examples is purely illustrative and they are not intended in any way to limit the scope of the present invention, as indicated in the accompanying claims.

EXAMPLE 1

5 volumes of a solution of rGOα in 50 mM Hepes, pH 8, 1 mM EDTA, 1 mM DTT and 0.02% of Lubrol (HEDL) were mixed with 1 volume of the same buffer containing 0.84% of sodium cholate, 0.05% of dimyristoyl-L-α-phosphatidylcholine, 0.05% of phosphatidylethanolamine from bovine brain and 0.067% of phosphatidyl-serine from bovine brain (as described by Mousli et al., 1990, Immunol. Lett., 25, 355–358) and preincubated at 4° C. overnight.

An aliquot of 32 µl of this solution was incubated at 20° C. for 5 min in a final volume of 50 µl of HEDL containing 1.1 mM MgCl$_2$ and 0.4 µM ($\gamma^{-32}$p) GTP (10000–30000 cpm/pmol) and the respective peptide at the final concentrations indicated.

The reactions were terminated by adding 750 µl of a 5% suspension of vegetable charcoal in 20 mM phosphoric acid. After agitation and centrifuging, 400 µl of supernatant containing the radioactive phosphate were counted by liquid scintillation.

Mastoparan and peptides 4 (SEQ ID NO:4) and 8 (SEQ ID NO:8) were assayed under the aforesaid conditions. The results are shown in FIGS. 1 and 2.

Mastoparan (MP) and peptides 4 (SEQ. ID NO:4) and 8 (SEQ ID NO:8) stimulate the GTPase activity of rGOα in a manner dependent on the concentration. In the presence of 1 mM of peptide (concentration beyond which the peptides have no additional effect), GTP hydrolysis increased by 5 times in the case of MP and peptide 8 (SEQ ID NO:8) and 4 (SEQ ID NO:4) times in the case of peptide 4. 50 % of maximum stimulation is obtained at 500 µM concentration with MP and peptide 4 (SEQ ID NO:4), and at 250 µM concentration with peptide 8 (SEQ ID NO:8), which is therefore the most potent. There is no GTP hydrolysis if rGOα is absent or when the peptides are incubated with a control protein (such as albumin).

EXAMPLE 2

Peptides 1 (SEQ ID NO:1) 2 (SEQ ID NO:2) and 7 (SEQ ID NO:7) were assayed under the experimental conditions described in Example 1. The results are shown in FIG. 3.

The basal GTPase activity of rGOα is inhibited by peptides 1 (SEQ ID NO:1), 2 (SEQ ID NO:2) and 7 (SEQ ID NO:7). Peptide 2 (SEQ ID NO:2) is the most potent with an IC 50 (concentration necessary to achieve 50% inhibition) of 130 µM, and with an inhibitory effect exceeding 90% at 1 mM concentration. The IC 50 values for peptides 1 (SEQ ID NO:1) and 7 (SEQ ID NO:7) are 215 and 600 µM respectively. At 1 mM, hydrolysis of GTP by rGOα is inhibited by 75% in the case of peptide 1 (SEQ ID NO:1) and by 63% in the case of peptide 7 (SEQ ID NO:7).

EXAMPLE 3

Peptides 3 (SEQ ID NO:3), 5 (SEQ ID NO:5), 6 (SEQ ID NO:6) and 9 (SEQ ID NO:9) were assayed under the experimental conditions described in Example 1.

The peptides have no or only negligible effect on the hydrolysis of GTP by rGOα.

We claim:

1. A peptide consisting of a formula selected from the group consisting of:

Ala-Leu-Ala-Ile-Lys-Leu-Ile-Leu-Asn-Leu-Lys-Ala-Lys-Ala (SEQ ID NO.1), Leu-Lys-Ile-Ala-Leu-Asn-Leu-Lys-Ala-Leu-Ile-Ala-Ala-Lys (SEQ ID NO.2) and Leu-Asn-Ala-Lys-Leu-Lys-Ala-Ile-Ala-Leu-Ala-Leu-Ile-Lys (SEQ ID NO.7).

2. The peptide of claim 1, consisting of the formula: Ala-Leu-Ala-Ile-Lys-Leu-Ile-Leu-Asn-Leu-Lys-Ala-Lys-Ala (SEQ ID NO.1).

3. The peptide of claim 1, consisting of the formula: Leu-Lys-Ile-Ala-Leu-Asn-Leu-Lys-Ala-Leu-Ile-Ala-Ala-Lys (SEQ ID NO.2).

4. The peptide of claim 1, consisting of the formula: Leu-Asn-Ala-Lys-Leu-Lys-Ala-Ile-Ala-Leu-Ala-Leu-Ile-Lys (SEQ ID NO.7).

\* \* \* \* \*